united States Patent [19]
Pearce

[11] 4,303,584
[45] Dec. 1, 1981

[54] METHOD OF PREPARING VINCRISTINE
[75] Inventor: Homer L. Pearce, Indianapolis, Ind.
[73] Assignee: Eli Lilly and Company, Indianapolis, Ind.
[21] Appl. No.: 136,616
[22] Filed: Apr. 2, 1980
[51] Int. Cl.$^3$ ............................................ C07D 519/04
[52] U.S. Cl. .................................................. 260/244.4
[58] Field of Search ...................................... 260/244.4
[56] References Cited
U.S. PATENT DOCUMENTS
3,354,163  11/1967  Gorman ........................... 546/244.4

OTHER PUBLICATIONS
Fieser et al., Reagents for Organic Synthesis, John Wiley & Sons, New York, (1967), pp. 472–474.

Groves et al., J. Am. Chem. Soc., 96:16, pp. 5274–5275, 8/7/74.
Groves et al., J. Am. Chem. Soc., 97:24, pp. 7118–7122, 11/26/75.
Groves et al., J. Am. Chem. Soc., 98:3, pp. 859–861, 2/4/76.
Groves et al., J. Am. Chem. Soc., 98:17, pp. 5290–5291, 8/18/76.

Primary Examiner—Donald G. Daus
Assistant Examiner—Diana G. Rivers
Attorney, Agent, or Firm—James L. Rowe; Arthur R. Whale

[57] ABSTRACT

Vincristine is prepared from VLB sulfate or free base by oxidation with an acidic ferrous perchlorate-hydrogen peroxide oxidation reagent at about −30° C.

5 Claims, No Drawings

METHOD OF PREPARING VINCRISTINE

BACKGROUND OF THE INVENTION

The alkaloids obtainable from *Vinca rosea* represent one of the most productive research areas among those groups of drugs which adversely affect the growth of experimental malignancies in mammals. Initially, only some of the alkaloids obtainable from the leaves of the plant by extraction and chromatography were found to be active as oncolytic agents. It was determined that these active anti-neoplastic vinca alkaloids obtained directly from the plant were dimeric indole-dihydroindole alkaloids representable by the formula:

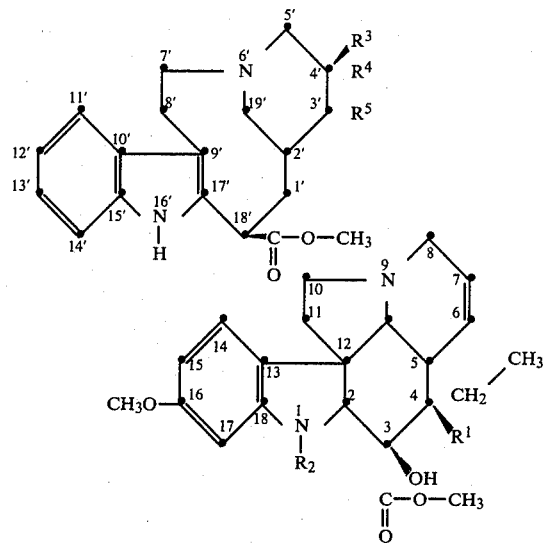

I

In the above formula where $R^1$ is acetoxy, $R^2$ is methyl, $R^3$ is hydroxyl, $R^4$ is ethyl and $R^5$ is H, VLB (vincaleucoblastine, vinblastine) is represented; where $R^1$ is acetoxy, $R^2$ is formyl, $R^3$ is hydroxyl, $R^4$ is ethyl and $R^5$ is H, vincristine (VCR, leurocristine) is represented; where $R^1$ is acetoxy, $R^2$ is methyl, $R^3$ is ethyl, $R^4$ is hydroxyl, and $R^5$ is H, leurosidine (vinrosidine) is represented; where $R^1$ is acetoxy, $R^2$ is methyl or formyl, $R^3$ is ethyl and $R^4$ and $R^5$ taken together form an α-epoxide ring, leurosine and leuroformine, respectively are represented. Literature references to the above alkaloids are as follows: leurosine (U.S. Pat. No. 3,370,057), VLB (U.S. Pat. No. 3,097,137), leuroformine (Belgian Pat. No. 811,110); leurosidine and leurocristine (both in U.S. Pat. No. 3,205,220).

Two of the above alkaloids, VLB and vincristine, are now marketed for the treatment of malignancies, particularly the leukemias and related diseases in humans. The two marketed alkaloids are customarily administered by the i.v. route. Two others, leurosidine and leuroformine, have been on clinical trial, either in the U.S. or in Europe.

VLB is the more abundant of the marketed alkaloids, being isolable in usually ten-fold greater quantity than vincristine. However, on a weight basis, the dose of vincristine employed in humans is about ⅛ to ⅓ that of VLB. Methods of converting VLB to vincristine are, therefore, highly desirable, and much research and considerable resources have been expended looking for such procedures. To date, only three methods of converting VLB to vincristine have appeared in the literature. These are; enzymatic oxidation with a peroxidase and $H_2O_2$, (Gorman-U.S. Pat. No. 3,354,163); catalytic oxidation with molecular oxygen at ambient temperature in formic acid (Derwent Abstract 33812Y/19-based on Soviet Union Pat. No. 521,845); and oxidation with chromic oxide in glacial acetic acid and acetone at $-60°$ C. (U.S. Pat. No. 3,899,943). In the patent, vincristine yields of 50% based on recovered VLB are reported. This oxidation process is not without drawbacks, however. The maintenance of a low reaction temperature is difficult in a manufacturing plant; but higher temperatures are found to produce increasing quantities of undesirable by-products. In addition, Barnett et al., U.S. Pat. No. 4,110,330, have found that VLB reacts with acetone at C-5' under oxidizing conditions even at $-60°$ C. 5'-acetonyl VLB and a related dehydration product constitute undesirable by-products of the chromic acid oxidation procedure in acetone since the 5'-acetonyl compound must be separated from vincristine by chromatography, with consequent mechanical loss of desired products. Furthermore, substantial quantities of N-desformyl vincristine are produced by chromic oxide oxidation even at low temperatures. This desformyl material must be reformylated in order to maximize vincristing yields. Reformylation is an added, necessary procedure where oxidation with chromic acid results in deformylation of the oxidized product.

The perchloric acid-ferrous perchlorate hydrogen peroxide oxidation reagent and its use is described in a series of papers by Groves et al., *J. Am. Chem. Soc.*, 96 5274 (1974); 97 7118 (1975); and 98 859, 5290 (1976).

It is an object of this invention to provide an oxidation procedure for converting VLB to vincristine which avoids the drawbacks of the prior art procedures.

DESCRIPTION OF THE INVENTION

In fulfillment of the above and other object, this invention provides a method for oxidizing VLB to vincristine using a combination of an iron salt, an acid and hydrogen peroxide as the oxidizing medium. The reaction is carried out in an inert mutual solvent, preferably acetonitrile, a temperature in the range $-20°$ to $-40°$ C. The preferred iron salt is ferrous perchlorate.

The following specific examples illustrate the process of this invention.

EXAMPLE 1

A stirred solution of 170 mg. of ferrous perchlorate hexahydrate in 1.5 ml. of acetonitrile was degassed with nitrogen while cooling to about $-20°$ C. A mixture of 142 mg. of VLB sulfate in 1 ml. of acetonitrile was mixed with 0.135 ml. of 70% perchloric acid at ambient temperature. This solution was added to the chilled solution of ferrous perchlorate. The reaction mixture turned a clear greenish brown. A degassed solution of 1.22 ml. of 30% hydrogen peroxide in 10 ml. of acetonitrile was added to the VLB sulfate-perchlorate-perchloric acid solution over a 25 minute period while maintaining the temperature to about $-20°$ C. After the addition had been completed, the reaction mixture was stirred for an additional 20 minutes and then quenched by the addition of 1 ml. of 15% aqueous sodium bisulfite. The resulting mixture was stirred for an additional 10 minutes and then added to 10 ml. of 14M aqueous ammonium hydroxide chilled to about 0° C. The volume of the mixture was increased to 30 ml. by the addition of methylenedichloride. The organic layer was separated and the aqueous layer extracted with 15 ml. of methylenedichloride. The organic extracts were combined and the combined extracts washed once with 10 ml. of 14M aqueous ammonium hydroxide and then four times with 10 ml. of a pH 7 phosphate buffer followed by one wash with 10 ml. of saturated aqueous sodium chloride. The organic layer was dried and the solvents evaporated therefrom in vacuo. The residue, consisting of 12 mg. of a dark red oil, was purified by preparative thin layer chromatography using four silica-coated plates (20×20×0.025 cm.). The chromatogram was developed at 0° C. with methylenedichloride containing 10% methanol. Bands corresponding to vincristine were removed manually and yielded 14 mg. of a pink glass which had the physical characteristics of vincristine free base.

EXAMPLE 2

One hundred four milligrams of VLB sulfate were dissolved in 5 ml. of acetonitrile. The reaction mixture was cooled to about −20° C. while being degassed with nitrogen. A mixture of 249 mg. of ferrous perchlorate and 0.1 ml. of 70% perchloric acid was added thereto. Next, to the stirred solution maintained at −20° C., 0.22 ml. of 30% hydrogen peroxide and 1 ml. of acetonitrile were added over a 20 minute period. The reaction mixture was stirred for an additional 15 minutes at −20° C. and, after cooling to about −60° C. with a dry ice-acetone bath, was then quenched by the addition of 5 ml. of 14M aqueous ammonium hydroxide. Next, 1 ml. of 15% aqueous sodium bisulfite was added. The mixture was filtered and the filter pad washed with 40 ml. of methylenedichloride. The organic filtrate was washed twice with 20 ml. portions of 14M ammonium hydroxide and three times with a pH 7 phosphate buffer. The organic layer was then dried and the solvents evaporated therefrom in vacuo. 65 mg. of a crude red oil comprising vincristine were obtained. The crude vincristine was applied to three 20×20×0.025 cm. preparative thin layer chromatographic plates coated with silica. The chromatogram was developed at 0° C. with methylenedichloride containing 10% methanol and 3% isopropanol. 0.6 mg. of vincristine were isolated from one of these plates plus 3.0 mg. of vincristine N-oxide. The N-oxide can be converted to vincristine by an additional sodium metabisulfite wash.

EXAMPLE 3

A solution of 100 mg. of VLB free base in 1.5 ml. of acetonitrile was placed in a 25 ml. round-bottom flask, and cooled to a temperature in the range −30° C. to −35° C. The flask was degassed and flushed with $N_2$. 268 mg. of ferrous perchlorate hexahydrate were added and the flask again degassed and flushed with $N_2$. 0.18 ml. of glacial acetic acid were added followed by the addition over a 15 minute period of one ml. of a 10% hydrogen peroxide in acetonitrile solution (prepared by placing 0.13 ml. of 30% $H_2O_2$ in water in a 10 ml. graduate and adding acetonitrile to 10 ml.). The reaction mixture was stirred for 3 hours at a reaction temperature of about −32° C. One gram of HYFLO SUPER-CEL ® (a diatomaceous earth filter aid) was added followed by 1.5 ml. of 14N aqueous ammonium hydroxide and 1.5 ml. of 15% aqueous solution bisulfite. The reaction mixture was allowed to warm to ambient temperature with stirring and was then filtered. The filtrate was extracted twice with 50 ml. portions of $CH_2Cl_2$ and once with 40 ml. of $CH_2Cl_2$. The organic extracts were combined and the combined extracts washed with 30 ml. of saturated aqueous sodium chloride. The organic layer was dried and the volatile constituents removed by evaporation in vacuo, leaving a brownish-red residue comprising vincristine produced in the above oxidation; weight=88.3 mg. Chromatography of the residue over 5.1 g. of silica gel was carried out. The chromatogram was developed with $CH_2Cl_2$ containing increasing amounts (1–8%) of methanol. Fractions shown to contain vincristine by TLC were combined. Evaporation of the solvent yielded 36.4 g. of vincristine fractions assayed to be about 75% pure.

Following the above procedure, yields as high as 35% of vincristine based upon VLB free base have been obtained.

The fact that the oxidation carried out from about −30° C. to −35° C. rather than at −60° C. as with the chromic oxide-sulfuric acid oxidation, confers a definite advantage on my novel process. In addition, under the reaction conditions, the solvent, acetonitrile, does not react with the VLB or vincristine, as does acetone in the standard chromic acid-sulfuric acid oxidation.

Vincristine prepared by the above oxidation procedure can be purified to that degree necessary for use an an intravenous drug by chromatography over silica or alumina or a combination of both or by crystallization.

The iron salt-hydrogen peroxide mixture is employed in conjunction with an acid such as perchloric, acetic or sulfuric acids. I prefer to use glacial acetic acid for this purpose.

I have preferred to use acetonitrile as the reaction solvent. However, any solvent with a suitably low coordination or chelating power for iron, such as acetonitrile, can be used. I have also preferred to use ferrous perchlorate as the perchlorate salt.

I claim:

1. The process for preparing vincristine which comprises oxidizing a solution of vinblastine sulfate at a temperature in the range about −20° C. to about −40° C. with an acidic ferrous salt-hydrogen peroxide oxidizing mixture, making the reaction mixture strongly basic, extracting therefrom the vincristine thus produced with an organic solvent and then isolating the vincristine.

2. A process according to claim 1 in which the iron salt is ferrous perchlorate.

3. A process according to claim 1 in which the acid used with the oxidizing mixture of an iron salt and hydrogen peroxide is glacial acetic acid.

4. A process according to claim 1 in which the solvent for vinblastine has a low coordinating power for iron.

5. A process according to claim 1 in which the solvent is acetonitrile.

* * * * *